United States Patent
Tamburrino et al.

(12)

(10) Patent No.: US 6,483,535 B1
(45) Date of Patent: Nov. 19, 2002

(54) WIDE ANGLE LENS SYSTEM FOR ELECTRONIC IMAGERS HAVING LONG EXIT PUPIL DISTANCES

(75) Inventors: Richard A. Tamburrino; Raymond A. Lia, both of Auburn; Dominick Danna, Syracuse, all of NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/471,849

(22) Filed: Dec. 23, 1999

(51) Int. Cl.[7] .................................................. H04N 7/18
(52) U.S. Cl. ......................................... 348/66; 348/345
(58) Field of Search ............................ 348/66, 86, 345; H04N 7/18

(56) References Cited

U.S. PATENT DOCUMENTS 5,384,231 A    1/1995   Johnson
5,731,899 A    3/1998   Meyers
5,781,807 A    7/1998   Glassgold et al.
5,796,522 A    8/1998   Meyers
5,812,322 A    9/1998   Meyers
5,822,125 A    10/1998  Meyers

*Primary Examiner*—Young Lee
(74) *Attorney, Agent, or Firm*—Wall Marjama & Bilinski LLP

(57) ABSTRACT

An imaging assembly includes a miniature electronic image sensor including an imaging substrate having a plurality of pixels and a microlens array aligned with corresponding pixels on said imaging substrate and focusing optics for focusing an optical image of a target onto the imaging substrate including at least one adaptive lens element. The focusing optics have a first exit pupil distance defining a first field of view and the miniature electronic image sensor has a second exit pupil distance defining a second field of view which is different than the first exit pupil distance. The adaptive lens element directs light onto said imaging substrate through said microlens array while maintaining the first field of view.

6 Claims, 3 Drawing Sheets

WIDE ANGLE LENS SYSTEM FOR ELECTRONIC IMAGERS HAVING LONG EXIT PUPIL DISTANCES

FIELD OF THE INVENTION

This invention relates to electronic imaging systems, and more particularly to a wide angle lens system which compensates a solid state electronic image sensor having a long exit pupil distance.

BACKGROUND OF THE INVENTION

In the construct of electronic video imaging systems, it is desirable to be able to effectively focus incoming light received from a target onto the imaging substrate of an electronic image sensor, such as a Charge Coupled Device (CCD).

Certain diagnostic instruments such as borescopes and endoscopes used for industrial and medical applications, respectively, include optical focusing systems having a relatively short exit pupil distance (E.P.D.) on the order of approximately 2 to 6 mm which produces a relatively wide field of view (e.g., 50°–70°). Conversely, miniature electronic image imagers for video camcorders, hand-held photographic digital cameras, and the like which are mass manufactured by the Eastman Kodak Company and the Sony Corporation, among others, are typically designed with a long E.P.D. of about 20 to 30 mm, producing a comparatively narrow field of view of about 10°–20°.

Emphasis on compactness of design is especially important to resolving issues such as comfort for the patient in the case of medical endoscopic devices, and ease in allowing the instrument to traverse a narrow cavity, such as a pressure vessel, in the case of industrial borescopes. Therefore, considerable interest is maintained in reducing the size of the electronic imager. Size reductions in some, however, accentuate the mismatch between the electronic imager and the focusing optics of the device in that the picture brightness is increasingly attenuated as a function of the radial distance from the center of the field of view. The angle of the light rays propagating from the focusing lens to the microlens array of the imager does not fully strike the corresponding pixels on the CCD. This attenuation causes undesired flicker in the processed video image. solid state image sensors, such as CCDs or further including CMOS-type imagers, can be designed with shorter EPDs to compensate for the above noted mismatches, such devices are not commonly manufactured, and therefore would significantly increase associated costs.

SUMMARY OF THE INVENTION

It is therefore a primary object of the present invention to improve the state of the art of electronic imaging systems.

It is a further object of the present invention to alleviate potential mismatches between solid state imagers having long exit pupil distances and optical devices such as borescopes and endoscopes, that require a wider field of view.

Therefore, and according to a preferred aspect of the invention, there is described an imaging assembly comprising:

a miniature electronic image sensor including an imaging substrate having a plurality of pixels and a microlens array aligned with corresponding pixels on said imaging substrate; and focusing optics for focusing an optical image of a target onto said imaging substrate including at least one adaptive lens element, in which said focusing optics have a first exit pupil distance defining a first field of view and said electronic image sensor has a second exit pupil distance defining a second field of view, the first exit pupil distance being different from the second exit pupil distance, and in which said adaptive lens element directs light onto said imaging substrate through said microlens array while permitting the imaging assembly to maintain the first field of view.

Preferably, the adaptive lens element(s) are existing lenses within the focusing optics having adequate power to cause light rays in the imaging plane to enter the lenslet array at approximately the same angle as the rays which would have entered for focusing optics of a system set for an image sensor having a longer exit pupil distance (EPD) than that of the focusing optics.

According to another preferred aspect of the present invention, there is disclosed an intraoral dental camera including:

a housing and a camera head disposed at a distal end of said housing, and in which the camera head includes an imaging assembly comprising:

a miniature electronic image sensor having a plurality of pixels arranged on an imaging substrate and an array of microlenses aligned with corresponding pixels on said imaging substrate; and focusing optics for focusing an optical image of a target onto said imaging substrate, said focusing optics including at least one adaptive lens element, wherein said focusing optics has a first exit pupil distance defining a first field of view and the image sensor has a second exit pupil distance defining a second field of view, wherein said at least one adaptive lens element directs light to the microlens array from a target while maintaining the field of view of the focusing optics.

Though preferably the camera head imaging assembly is configured to configure a long EPD image sensor with focusing optics having a smaller EPD (a wider field of view), an adaptive lens element can similarly be configured for use with an image sensor having a smaller EPD than that of the focusing optics.

An advantage of the present invention is that miniature electronic image sensors with long EPDs, such as those which are more commonly mass produced for use in video camcorders, hand-held photographic digicams, and the like, can more easily be incorporated into endoscopic and borescopic devices, such as intraoral dental cameras, which require a substantially wider wide field of view than the former devices.

These and other objects, features and advantages will become apparent from the following Detailed Description when read in conjunction with the accompanying drawings.

DETAILED DESCRIPTION

The following relates to an adaptive optical element used to alleviate mismatches between miniature electronic image sensors having a long exit pupil distance (EPD) and the focusing optics of a typical medical or industrial inspection device, such as an endoscope or borescope.

Figure 1:
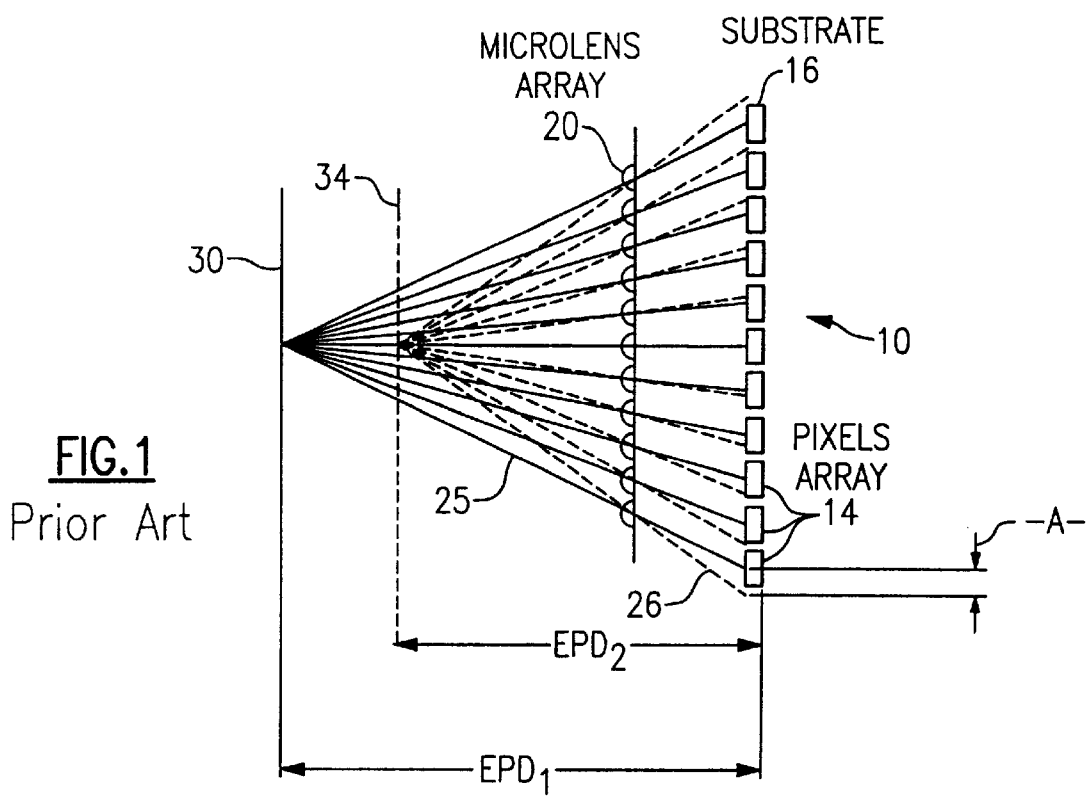
FIG. 1 is a prior art representation of a video imaging system illustrating a alignment mismatch between an electronic image sensor having a first EPD and focusing optics having a second EPD which is different than that of the image sensor.

FIG. 1 illustrates the problem to which the present invention is directed to. A miniature electronic image sensor 10 includes an array of pixels 14 (only one column of which is shown in FIG. 1) disposed on an imaging substrate 16 in a manner commonly known. The image sensor 10 further includes a microlens array 20 (only one corresponding column also being shown) aligned with the imaging substrate 16 and defining an exit pupil distance (hereinafter EPD (1)) between a principal imaging plane 30 and the imaging substrate 16. In this example, the miniature electronic image sensor 10 is a Sony Model ICX206AK, which is suitable for use in a video camcorder in which light rays, identified as 25, are ideally traced from the principal plane 30 onto the pixel array 14 through the microlens array 20.

The focusing optics of a typical medical diagnostic instrument, are contrasted in phantom in FIG. 1. The optics of the typical instrument define a principal plane 34 having a shorter EPD (EPD (2)) than that of the image sensor 10. The shorter EPD provides a larger field of view which is desired for the diagnostic device. Use of the optics therefore produce a misalignment of light rays 26 that pass through the microlens array 20 and are misaligned relative to the pixels 14. The misalignment, represented as -A- produces flicker in the resulting video image.

Figure 2:
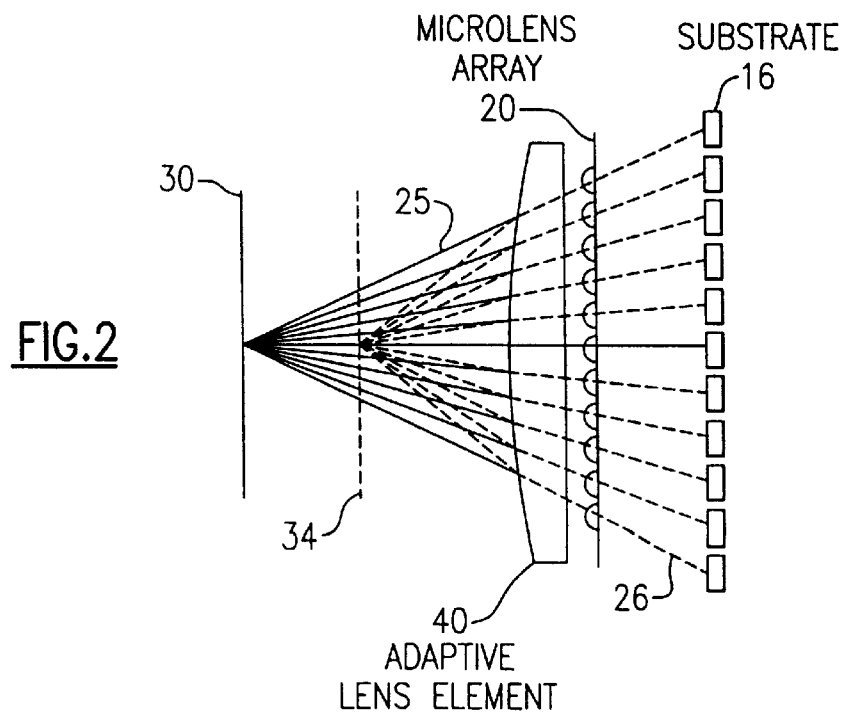
FIG. 2 is a representation of the video imaging system of FIG. 1, including an adaptive lens element made in accordance with a preferred aspect of the present invention.

Referring to FIG. 2, a comparison to that depicted in FIG. 1 is shown, including an adaptive lens element 40 which is introduced between the shorter principal plane 34 of the focusing optics of the medical or industrial diagnostic instrument and the miniature electronic image sensor 10. The adaptive lens element 40, described below, includes a convex lens having a selected radius of curvature which bends the incoming light rays inwardly to alleviate any misalignment relative to the pixel array 14. Therefore, the optical lens system of the instrument maintains the field of view presented by the shorter EPD(2) while still maintaining focus of the longer EPD image sensor 10.

Figure 3:
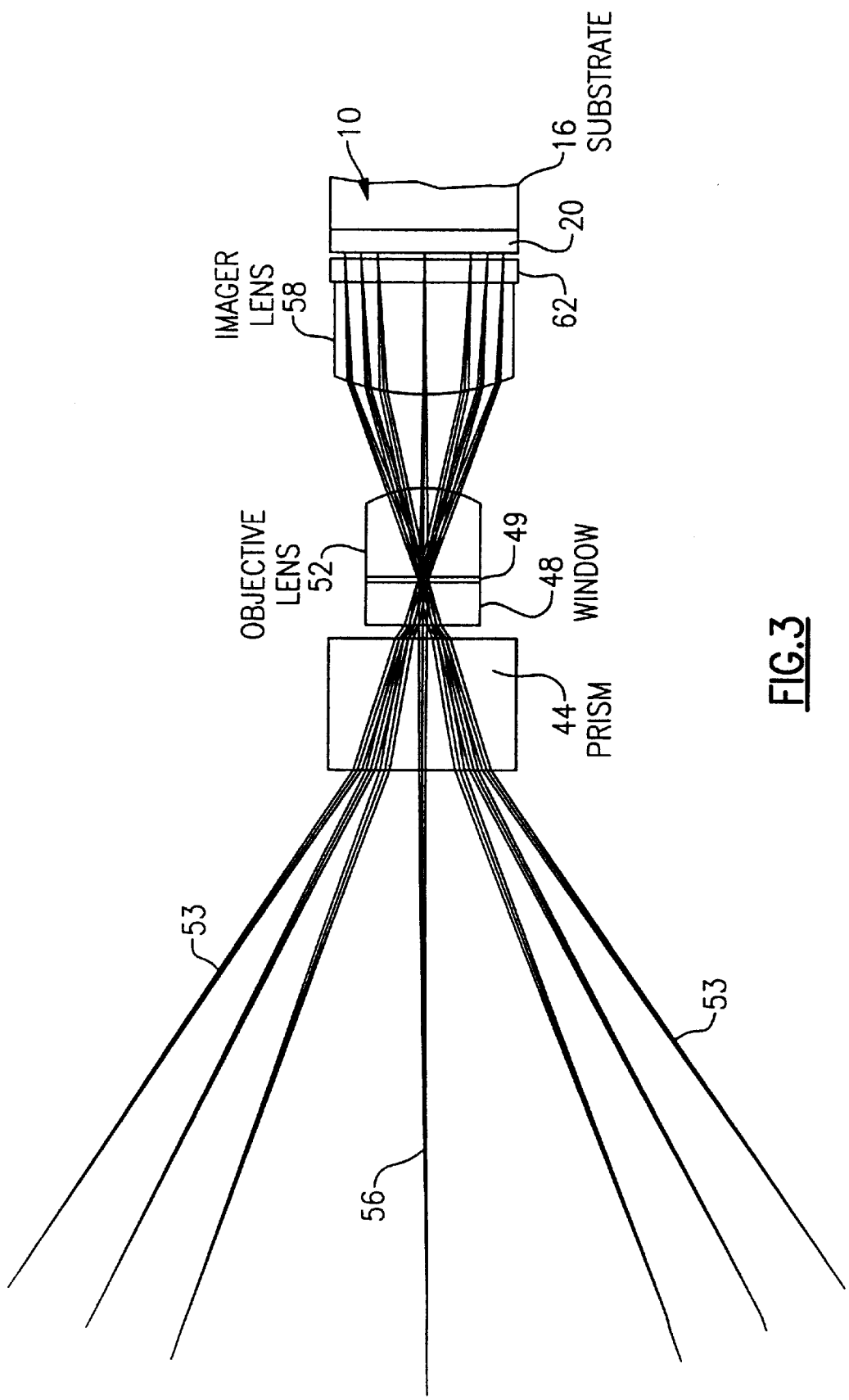
FIG. 3 is a partial representation of an optical system of a diagnostic viewing instrument having focusing optics which incorporate the concept of the adaptive lens element of FIG. 2.

Referring to FIG. 3, an optical system 50 of a diagnostic viewing instrument is shown schematically, the system including an unfolded prism 44 which receives incoming light rays 53 from a target (not shown) which is directed through an objective window 48. The incoming rays 53 are stopped down to an intermediate converging point by an aperture 49, through which the rays reemerge and are directed through focusing optics comprising an objective lens 52 and an imager lens 58, each of which are commonly aligned along an imaging axis 56. The imager lens 58 is defined with an appropriate radius of curvature which inwardly bends the rays 53 and directs the rays with minimum distortion through a window 62 in an aligned manner through the microlens array 20 and subsequently onto the imaging substrate 16 of the image sensor 10 (shown partially). According to the embodiment shown, the adaptive focusing optics produce an angular deviation of the incoming light rays 53 of approximately 4.8 degrees with respect to the imaging axis 56. As noted, this angular deviation is suitable to align the rays such that they impinge onto the pixels 14 of the image sensor 10. In the meantime, described imaging system allows the miniature electronic image sensor 10, having a large EPD, to be used in a short exit pupil distance system while maintaining the principal plane 34, like that shown schematically in FIG. 2.

Figure 4:
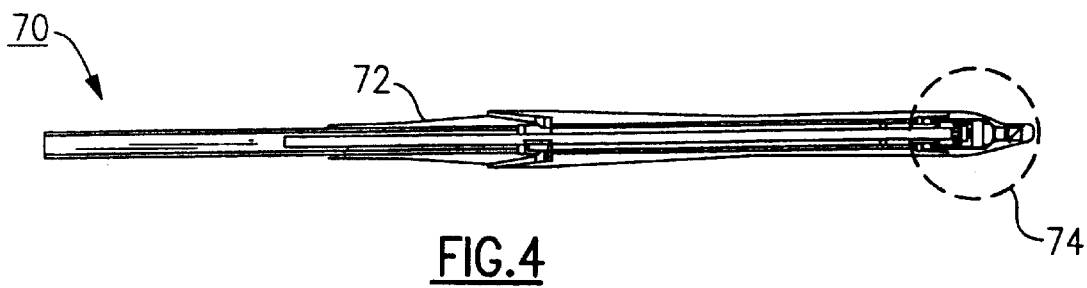
FIG. 4 is a partial perspective view in section of a dental intraoral camera including a wide angle lens system made in accordance with the present invention.
Figure 5:
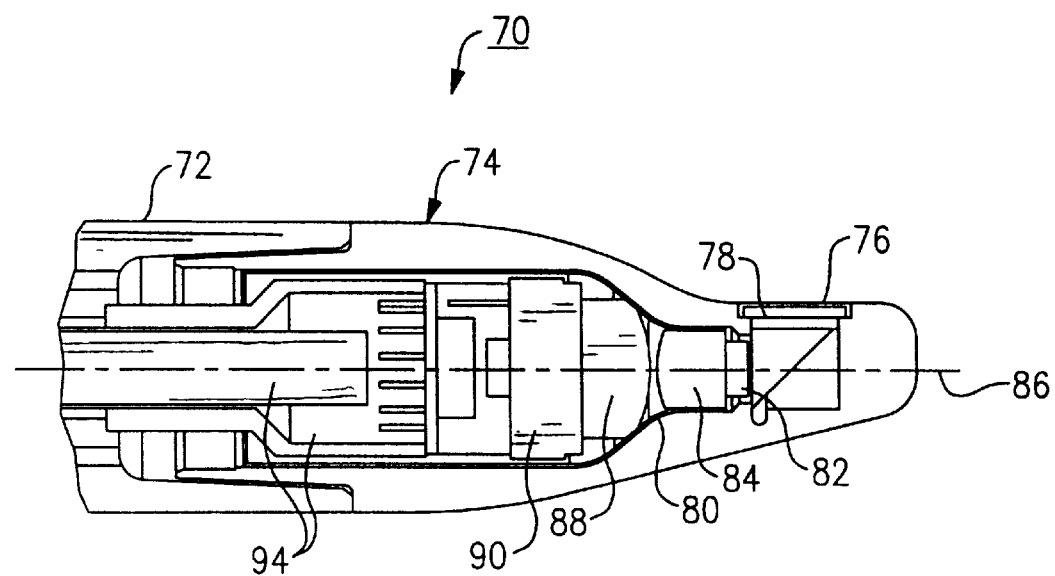
FIG. 5 is an enlarged sectional view of the distal camera head portion of the intraoral dental camera of FIG. 4.

Referring to FIGS. 4 and 5, an optical system incorporating the above concepts are provided for a dental intraoral camera 70. The intraoral camera 70 according to this embodiment includes a cylindrically shaped housing or handle 72, partially shown, having a distally arranged camera head 74. The specific optical system includes a sapphire or other viewing window 76 disposed within the distal camera head 74 which is positioned adjacent a 90 degree prism 78 to allow side viewing of a dental target. A lens cell 80 proximally disposed relative to the prism 78 contains a number of optical elements in a fixed relation including an objective window 82 and an objective lens 84, each of which are commonly aligned along an imaging or viewing axis 86 and defining an aperture stop (not shown) therebetween. An imager lens 88 is also fixedly maintained and aligned within the lens cell 80 along an imaging axis 86 in front of the imaging substrate and the microlens array of a miniature electronic image sensor 10.

More specifically with regard to the described embodiment, the image sensor 90 is a Sony Model ICX206AK having a exit pupil distance of about 25 mm, while the focusing optics of the above wide angle lens system have an exit pupil distance of about 6 mm defining a field of view of about 76 degrees with the lens system having a focal length of about 3.5 mm. The objective lens 84 and the imaging lens 88 are each adapted to direct light suitably to the longer EPD image sensor 90 with the objective lens having an effective focal length of about 5.3 mm and the imaging lens having an equivalent focal length of about 7.4 mm.

The camera housing 72 or handle is an elongated cylindrical member and includes an electrical harness 94 which is proximally attached to an electronic image sensor 90 in a manner which is conventionally known. The electrical harness 94 includes a plurality of electrical conductors (not shown) which transmit an electrical signal from the electronic image sensor 90 for processing into a video signal for display onto a monitor (not shown). The harness 94 also includes power transmission cabling for powering the image sensor 10 and an associated light source. According to this embodiment, the light source can include an optical bundle of fibers extending from a remote light box (not shown) or contained lamp, or can include a plurality of white light emitting LEDs (not shown) disposed at the distal end of the camera head in relation to the viewing window 53.

PARTS LIST FOR FIGS. 1–5 miniature electronic image sensor
14 pixel array
16 imaging substrate
20 microlens array
30 principal plane
34 principal plane
40 adaptive optical element
44 prism
48 objective window
49 aperture stop
50 optical system
52 objective lens
53 light rays
56 imaging axis
58 imager lens 62 window
70 dental intraoral camera
72 housing
74 camera head
76 viewing window
78 prism
80 lens cell
82 objective window
84 objective lens
86 viewing axis
88 imager lens
90 image sensor
94 electrical harness Though the preceding has been described with regard to certain embodiments, it will be appreciated that certain modifications and variations of the inventive concepts are possible as defined by the following claims.

We claim:

1. An imaging assembly comprising:
    a miniature electronic image sensor including an imaging substrate having a plurality of pixels and a microlens array aligned with corresponding pixels on said imaging substrate;
    focusing optics for focusing an optical image of a target onto said imaging substrate including at least one adaptive lens element, in which said focusing optics have a first exit pupil distance defining a first field of view and said electronic image sensor has a second exit pupil distance defining a second field of view, the first exit pupil distance being different from the second exit pupil distance, and in which said adaptive lens element directs light onto said imaging substrate through said microlens array while permitting the imaging assembly to maintain the first field of view.

2. An imaging assembly as recited in claim 1, wherein said imaging assembly is used in an endoscope.

3. An imaging assembly as recited in claim 2, wherein said endoscope is an intraoral dental camera.

4. An imaging assembly as recited in claim 1, wherein the exit pupil distance of the image sensor is longer than the exit pupil distance of the focusing optics.

5. An intraoral dental camera as recited in claim 1, wherein the exit pupil distance of the image sensor is longer than the exit pupil distance of the focusing optics.

6. An intraoral dental camera including:
    a housing:
        a camera head disposed at a distal end of said housing, said camera head including an imaging assembly comprising:
            miniature electronic image sensor having a plurality of pixels arranged on an imaging substrate and an array of microlenses aligned with corresponding pixels on said imaging substrate; and
            focusing optics for focusing an optical image of a target onto said imaging substrate, said focusing optics including at least one adaptive lens element, wherein said focusing optics has a first exit pupil distance defining a first field of view and the image sensor has a second exit pupil distance defining a second field of view, wherein said at least one adaptive lens element directs light to the microlens array from a target while maintaining the field of view of the focusing optics.

* * * * *